(12) United States Patent
Page et al.

(10) Patent No.: US 11,345,882 B2
(45) Date of Patent: *May 31, 2022

(54) EXTRA-CAPILLARY FLUID CYCLING SYSTEM AND METHOD FOR A CELL CULTURE DEVICE

(71) Applicant: BIOVEST INTERNATIONAL, INC., Tampa, FL (US)

(72) Inventors: Darrell Paul Page, East Bethel, MN (US); Robert J. Wojciechowski, Forest Lake, MN (US); Martin Peder Crep, St. Paul, MN (US)

(73) Assignee: BIOVEST INTERNATIONAL, INC., Tampa, FL (US)

( * ) Notice: Subject to any disclaimer, the term of this patent is extended or adjusted under 35 U.S.C. 154(b) by 399 days.

This patent is subject to a terminal disclaimer.

(21) Appl. No.: 15/245,524

(22) Filed: Aug. 24, 2016

(65) Prior Publication Data

US 2016/0362652 A1 Dec. 15, 2016

Related U.S. Application Data

(63) Continuation of application No. 14/033,807, filed on Sep. 23, 2013, now Pat. No. 9,534,198, which is a
(Continued)

(51) Int. Cl.
*C12M 3/00* (2006.01)
*C12M 1/00* (2006.01)
(Continued)

(52) U.S. Cl.
CPC ............. *C12M 41/40* (2013.01); *A61K 35/12* (2013.01); *C12M 23/26* (2013.01); *C12M 23/28* (2013.01);
(Continued)

(58) Field of Classification Search
CPC ...... C12M 23/28; C12M 23/44; C12M 23/26; C12M 41/40
See application file for complete search history.

(56) References Cited

U.S. PATENT DOCUMENTS 3,148,624 A 9/1964 Baldwin
4,047,844 A 9/1977 Robinson
(Continued)

FOREIGN PATENT DOCUMENTS

EP 0164020 B1 8/1989
EP 1400691 A2 3/2004
(Continued)

OTHER PUBLICATIONS

Ghaderi, A. et al., "Preparation of anion-exchange resin from styrene-divinylbenzene copolymer obtained by concentrated emulsion polymerization method," *Iranian Polymer Journal*, 2006, vol. 15, pp. 497-504.
(Continued)

*Primary Examiner* — Nathan A Bowers
(74) *Attorney, Agent, or Firm* — Saliwanchik, Lloyd & Eisenschenk (57) ABSTRACT

An extra-capillary fluid cycling unit for maintaining and cycling fluid volumes in a cell culture chamber includes a housing and a first flexible reservoir extra-capillary fluid reservoir disposed in the housing. The extra-capillary fluid reservoir is in fluid communication with a cell culture chamber. A second flexible reservoir is also located in the housing, the second flexible reservoir being in fluid communication with a pressure source. A sensor plate is movably disposed in the housing between the extra-capillary reservoir and the second reservoir, wherein the second reservoir is pressurized to move the sensor plate in relation to the
(Continued)

extra-capillary reservoir to cause fluid cycling and maintain fluid volumes in the cell growth chamber.

13 Claims, 9 Drawing Sheets

Related U.S. Application Data continuation of application No. 12/274,971, filed on Nov. 20, 2008, now Pat. No. 8,540,499, which is a continuation-in-part of application No. PCT/US2007/012042, filed on May 21, 2007, and a continuation-in-part of application No. PCT/US2007/012051, filed on May 21, 2007, and a continuation-in-part of application No. PCT/US2007/012053, filed on May 21, 2007, and a continuation-in-part of application No. PCT/US2007/012052, filed on May 21, 2007, and a continuation-in-part of application No. PCT/US2007/012054, filed on May 21, 2007.

(60) Provisional application No. 60/802,376, filed on May 22, 2006.

(51) Int. Cl.
| | |
|---|---|
| C12M 1/34 | (2006.01) |
| F04B 43/12 | (2006.01) |
| A61K 35/12 | (2015.01) |
| C12M 1/26 | (2006.01) |
| C12M 1/02 | (2006.01) |
| C12M 1/36 | (2006.01) |
| F04B 43/00 | (2006.01) |
| C12M 1/12 | (2006.01) |
| C12Q 3/00 | (2006.01) |
| F04B 43/09 | (2006.01) |

(52) U.S. Cl.
CPC ............ *C12M 23/34* (2013.01); *C12M 23/44* (2013.01); *C12M 23/58* (2013.01); *C12M 25/10* (2013.01); *C12M 27/00* (2013.01); *C12M 29/00* (2013.01); *C12M 29/10* (2013.01); *C12M 29/18* (2013.01); *C12M 33/14* (2013.01); *C12M 41/20* (2013.01); *C12M 41/26* (2013.01); *C12M 41/34* (2013.01); *C12M 41/38* (2013.01); *C12M 41/48* (2013.01); *C12M 47/02* (2013.01); *C12M 47/04* (2013.01); *C12M 47/10* (2013.01); *C12M 47/20* (2013.01); *C12Q 3/00* (2013.01); *F04B 43/0072* (2013.01); *F04B 43/09* (2013.01); *F04B 43/12* (2013.01); *F04B 43/1292* (2013.01)

(56) References Cited

U.S. PATENT DOCUMENTS

| | | | |
|---|---|---|---|
| 4,167,046 A * | 9/1979 | Portner | A61M 1/122 |
| | | | 128/899 |
| 4,282,902 A | 8/1981 | Haynes | |
| 4,417,861 A | 11/1983 | Tolbert | |
| 4,604,038 A | 8/1986 | Belew | |
| 4,804,628 A | 2/1989 | Cracauer et al. | |
| 4,973,558 A | 11/1990 | Wilson et al. | |
| 5,113,906 A | 5/1992 | Högner | |
| 5,318,413 A | 6/1994 | Bertoncini | |
| 5,330,915 A | 7/1994 | Wilson et al. | |
| 5,416,022 A | 5/1995 | Amiot | |
| 5,541,105 A | 7/1996 | Melink et al. | |
| 5,554,123 A | 9/1996 | Herskowitz et al. | |
| 5,571,720 A | 11/1996 | Grandics et al. | |
| 5,622,857 A | 4/1997 | Goffe | |
| 5,631,006 A | 5/1997 | Melink et al. | |
| 5,656,421 A | 8/1997 | Gebhard et al. | |
| 5,958,763 A | 9/1999 | Goffe | |
| 5,998,184 A | 12/1999 | Shi | |
| 6,001,585 A | 12/1999 | Gramer | |
| 6,193,783 B1 * | 2/2001 | Sakamoto | B01D 19/0063 |
| | | | 95/247 |
| 6,733,252 B2 | 5/2004 | Feygin et al. | |
| 7,377,686 B2 | 5/2008 | Hubbard | |
| 7,654,982 B2 | 2/2010 | Carlisle et al. | |
| 7,935,504 B2 | 5/2011 | Chen | |
| 8,133,042 B2 | 3/2012 | Yajima | |
| 8,383,397 B2 | 2/2013 | Wojciechowski et al. | |
| 8,540,499 B2 | 9/2013 | Page et al. | |
| 9,441,195 B2 | 9/2016 | Wojciechowski et al. | |
| 2003/0040104 A1 | 2/2003 | Barbera-Guillem | |
| 2003/0217957 A1 | 11/2003 | Bowman, Jr. et al. | |
| 2004/0057856 A1 | 3/2004 | Saxer et al. | |
| 2006/0016487 A1 | 1/2006 | Lin | |
| 2006/0141623 A1 | 6/2006 | Smith et al. | |
| 2006/0257998 A1 | 11/2006 | Klaus et al. | |
| 2007/0062872 A1 | 3/2007 | Parker et al. | |
| 2007/0148010 A1 | 6/2007 | Michels et al. | |
| 2007/0292410 A1 | 12/2007 | Cashman et al. | |
| 2008/0017194 A1 | 1/2008 | Hassanein et al. | |
| 2009/0269841 A1 | 10/2009 | Wojciechowski et al. | |
| 2010/0015696 A1 | 1/2010 | Claes et al. | |
| 2010/0105138 A1 | 4/2010 | Dodd et al. | |
| 2011/0212493 A1 | 9/2011 | Hirschel et al. | |
| 2012/0086657 A1 | 4/2012 | Stanton, IV et al. | |
| 2012/0114634 A1 | 5/2012 | Stergiou et al. | |
| 2013/0058907 A1 | 3/2013 | Wojciechowski et al. | |
| 2014/0024012 A1 | 1/2014 | Page et al. | |
| 2015/0111252 A1 | 4/2015 | Hirschel et al. | |
| 2015/0225685 A1 | 8/2015 | Hirschel et al. | |
| 2016/0362650 A1 | 12/2016 | Wojciechowski et al. | |

FOREIGN PATENT DOCUMENTS

| | | |
|---|---|---|
| EP | 1 286 696 | 11/2006 |
| WO | WO 2002/087662 A1 | 11/2002 |
| WO | WO 2003/087292 A2 | 10/2003 |
| WO | WO 2005/031167 A1 | 4/2005 |
| WO | WO-2005/087915 | 9/2005 |
| WO | WO-2005/090403 | 9/2005 |
| WO | WO 2005/116186 A1 | 12/2005 |
| WO | WO 2007/136821 A1 | 11/2007 |
| WO | WO 2007/139742 A1 | 12/2007 |
| WO | WO 2007/139746 A1 | 12/2007 |
| WO | WO 2007/139747 A1 | 12/2007 |
| WO | WO 2007/139748 A2 | 12/2007 |
| WO | WO-2010/042644 | 4/2010 |
| WO | WO-2010/048417 | 4/2010 |
| WO | WO-2012/021840 | 2/2012 |
| WO | WO-2012/064760 | 5/2012 |
| WO | WO-2012/171026 | 12/2012 |
| WO | WO-2012/171030 | 12/2012 |
| WO | WO-2013/086418 | 6/2013 |
| WO | WO-2014/036187 | 3/2014 |

OTHER PUBLICATIONS

International Search Report dated Oct. 4, 2007 for International Patent Application No. PCT/US2007/012042, filed May 21, 2007, 2 pages.

International Search Report dated Oct. 5, 2007 for International Patent Application No. PCT/US2007/012051, filed May 21, 2007, 2 pages.

International Search Report dated Oct. 4, 2007 for International Patent Application No. PCT/US2007/012052, filed May 21, 2007, 2 pages.

International Search Report dated Nov. 7, 2007 for International Patent Application No. PCT/US2007/012053, filed May 21, 2007, 2 pages.

(56) References Cited

OTHER PUBLICATIONS

International Search Report dated Sep. 25, 2007 for International Patent Application No. PCT/US2007/012054, filed May 21, 2007, 3 pages.
Knazek, R. et al., "Cell Culture on Artificial Capillaries: An Approach to Tissue Growth in vitro," *Science*, 1972, vol. 178, No. 4056, pp. 65-67.
Natsume, A. et al., "Engineered Antibodies of IgG1/IgG3 Mixed Isotype with Enhanced Cytotoxic Activities," *Cancer Research*, 2008, vol. 68, No. 10, pp. 3863-3872.

* cited by examiner

EXTRA-CAPILLARY FLUID CYCLING SYSTEM AND METHOD FOR A CELL CULTURE DEVICE

CROSS-REFERENCE TO RELATED APPLICATIONS

This application is a continuation of: Application Ser. No. 14/033,807, filed Sep. 23, 2013, which is a continuation of:

Application Ser. No. 12/274,971, filed Nov. 20, 2008, now U.S. Pat. No. 8,540,499, which is a continuation-in-part of:

International Application No. PCT/US2007/012053, filed May 21, 2007, which claims the benefit under 35 USC § 119 of U.S. application Ser. No. 60/802,376, filed May 22, 2006, both of which are incorporated herein by reference in their entirety;

International Application No. PCT/US2007/012051, filed May 21, 2007, which claims the benefit of U.S. application Ser. No. 60/802,376, filed May 22, 2006, both of which are incorporated herein by reference in their entirety;

International Application No. PCT/US2007/012052, filed May 21, 2007, which claims the benefit of U.S. application Ser. No. 60/802,376, filed May 22, 2006, both of which are incorporated herein by reference in their entirety;

International Application No. PCT/US2007/012054, filed May 21, 2007, which claims the benefit of U.S. application Ser. No. 60/802,376, filed May 22, 2006, both of which are incorporated herein by reference in their entirety; and International Application No. PCT/US2007/012042, filed May 21, 2007, which claims the benefit of U.S. application Ser. No. 60/802,376, filed May 22, 2006; both of which are incorporated herein by reference in their entirety.

BACKGROUND OF THE INVENTION

Field of the Invention

The present invention relates to an extra-capillary (EC) fluid cycling system for a cell culture device, and more particularly to an EC cycling unit utilizing a non-rigid, EC reservoir fluidly connected to the cell culture device.

Description of the Related Art

The anticipated growth of personalized medicine will require new paradigms for the manufacture of therapies tailored to the needs of individual patients. The greatest challenge is expected to come in the area of cell based therapies, especially when such therapies are autologous in nature. In such cases each cell or cell based product will need to be manufactured from scratch for each patient. Manual methods for mammalian cell culture, by their nature, are prone to technician error or inconsistency leading to differences between supposed identical cultures. This becomes especially evident as more and more autologous cells are expanded for personalized therapies. Patient-specific cells, or proteins, are subject to variation, especially when scaled beyond levels that can be managed efficiently with manual methods.

In addition to being labor intensive, the stringent requirements for segregation of each patient's materials from that of every other patient will mean that manufacturing facilities will be large and complex, containing a multitude of isolation suites each with its own equipment (incubators, tissue culture hoods, centrifuges) that can be used for only one patient at a time. Because each patient's therapy is a new and unique product, patient specific manufacturing will also be labor intensive, requiring not just direct manufacturing personnel but also disproportionately increased manpower for quality assurance and quality control functions.

Moreover, conventional approaches and tools for manufacturing cells or cell based products typically involve numerous manual manipulations that are subject to variations even when conducted by skilled technicians. When used at the scale needed to manufacture hundreds or thousands of patient specific cell based therapies, the variability, error or contamination rate may become unacceptable for commercial processes.

Small quantities of secreted product are produced in a number of different ways. T-flasks, roller bottles, stirred bottles or cell bags are manual methods using incubators or warm-rooms to provide environments for cell growth and production. This method is very labor intensive, subject to mistakes and difficult for large scale production. Ascites production uses a host animal (usually a mouse) where the peritoneum is injected with the cells that express the product and are parasitically grown and maintained. The animals are sacrificed and the peritoneal fluid with the product is collected. This method is labor intense, difficult for large scale production and objectionable because of the use of animals. Another method is to inoculate and grow the cells in a small stirred tank or fermenter. The tank provides the environmental and metabolic needs and the cell secretions are allowed to accumulate. This method is costly in terms of facility support in order to do a large number of unique cells and produces product at low concentration.

Another method is to use a bioreactor (hollow fiber, ceramic matrix, fluidizer bed, etc) as the cell culture device in lieu of the stirred tank. This can bring facilities costs down and increases product concentration. Biovest International of Coon Rapids, Minn., has or had instruments using these technologies—hollow fiber, ceramic matrix, fluidized bed and stirred tanks.

Cell culturing devices or cultureware for culturing cells in vitro are known. As disclosed in U.S. Pat. No. 4,804,628, the entirety of which is hereby incorporated by reference, a hollow fiber culture device includes a plurality of hollow fiber membranes. Medium containing oxygen, nutrients, and other chemical stimuli is transported through the lumen of the hollow fiber membranes or capillaries and diffuses through the walls thereof into an extracapillary (EC) space between the membranes and the shell of the cartridge containing the hollow fibers. The cells that are to be maintained collect in the extracapillary space. Metabolic wastes are removed from the cultureware. The cells or cell products can be harvested from the device.

Known EC reservoirs have typically been rigid. They are a pressure vessel and therefore require a sealed compartment with tubing ports adding to costs. A gas, typically air, is introduced through a sterile barrier, generally a membrane filter, to control pressure in the vessel. Fluid level control has been limited to ultrasonic, conductive or optical trip points, or by a load cell measuring the weight of the fluid. Reservoirs are expensive and difficult to manufacture. There is limited EC fluid level measurement accuracy-ultrasonic, conductive or optical monitoring of fluid levels are commonly fouled by cell debris in the reservoir. Alternatively, load cells are not a rugged design for reliable fluid level sensing.

These methodologies rely on costly, labor intensive off-line sampling and analysis or additional equipment to interface with the instrument or require the addition of a lactate probe and electronics to the culture.

Preparing the system to start the cell culture is also very labor intensive. The cultureware must be assembled and sterilized or probes must be prepared, sterilized and aseptically inserted into the pre-sterilized portion of the cultureware. The cultureware assembly is then loaded onto the instrument. A series of manual operations are needed to check the integrity of the assembly, introduce fluid into the cultureware flow path, flush the toxic residuals from the cultureware, start the cultureware in a pre-inoculation mode, introduce factors into the flow path getting it ready for the cells, inoculating the cells into the bioreactor and starting the run (growth of the cell mass and eventual harvest of product).

Each unique cell or cell line must be cultured, cell products harvested and purified separately. In order to do a large number of unique cells or cell lines, a considerable number of instruments would be needed. If application of the cells or products for therapeutic purposes is contemplated strict segregation of each cell production process would be required. Consequently compactness of the design and the amount of ancillary support resources needed will become an important facilities issue. Moreover the systems currently available are general purpose in nature and require considerable time from trained operators to setup, load, flush, inoculate, run, harvest and unload. Each step usually requires manual documentation.

Accordingly, there is a need for an EC cycling device that is less expensive then the traditional rigid reservoirs and that provides accurate EC fluid level measurement.

SUMMARY OF THE INVENTION

One aspect of the present invention is to provide an EC fluid cycling unit that enables fluid level control without the use of expensive ultrasonics or load cells.

Another aspect of the present invention is to provide an EC cycling unit having increased EC fluid level measurement accuracy and decreased cell debris in the reservoir, as well as easier assembly.

Yet another aspect of the present invention is an EC cycling unit having a flexible reservoir.

Still another aspect of the present invention is to provide an EC cycling unit that costs less than rigid reservoirs. Also, a unit that has a sealed EC circuit design, without a vented reservoir, inhibits cell contamination.

According to these and other aspects of the present invention, there is provided an extra-capillary fluid cycling unit for maintaining and cycling fluid volumes in a cell culture chamber including a housing and a first flexible reservoir extra-capillary fluid reservoir disposed in the housing, the extra-capillary fluid reservoir being in fluid communication with a cell culture chamber. A second flexible reservoir is also located in the housing, the second flexible reservoir being in fluid communication with a pressure source. A sensor plate is movably disposed in the housing between the extra-capillary reservoir and the second reservoir, wherein the second reservoir is pressurized to move the sensor plate in relation to the extra-capillary reservoir to cause fluid cycling and maintain fluid volumes in the cell growth chamber.

According to these and other aspects of the present invention, there is also provided a method for extra-capillary fluid cycling in a cell culture chamber comprising the steps of providing an extra-capillary fluid cycling unit. The cycling unit including a housing, a first flexible extra-capillary fluid reservoir disposed in the housing, a second flexible reservoir located in the housing, and a sensor plate movably disposed in the housing between the extra-capillary reservoir and the second reservoir. A pressure source in communication with the second flexible reservoir is provided. A sensor in communication with the pressure source is also provided, wherein the sensor plate includes an indicator in communication with the sensor. The pressure source is activated to expand or contract the second reservoir. The sensor plate is moved to expand or contract the extra-capillary reservoir and the extra-capillary fluid is cycled through the cell culture chamber.

These and other features, aspects, and advantages of the present invention will become more apparent from the following detailed description of the preferred embodiment relative to the accompanied drawings, in which:

DETAILED DESCRIPTION OF THE PREFERRED EMBODIMENTS

Figure 1:
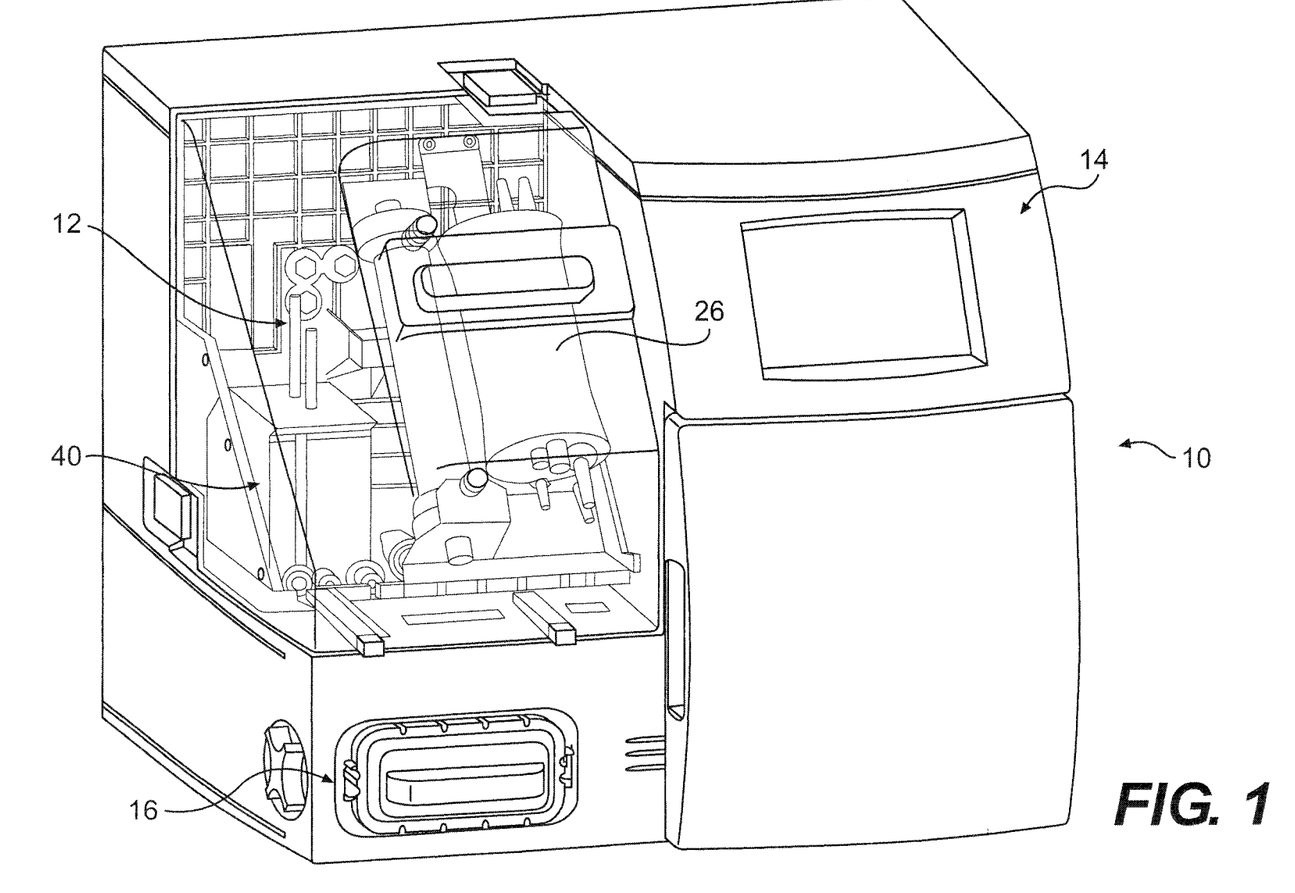
FIG. 1 is a perspective view of the system for producing cells and/or cell derived products according to the present invention.

Referring to FIG. 1, the present invention provides a fully integrated system 10 for producing cells and cell derived products in a closed, self-sufficient environment. More specifically, the system allows for cell expansion and harvest of cells and their products with minimal need for technician interaction. As will be described further herein, the device incorporates cell culture technology, for example, hollow fiber bioreactor perfusion technology, with all tubing components encased in a single-use, disposable incubator. Following bioreactor inoculation with cells, the system follows pre-programmed processes to deliver media, maintain pH, maintain lactate levels, control temperature and harvest cells or cell-secreted protein. Standard or unique cell culture methods can be programmed prior to bioreactor inoculation, such that, various cell types or proteins can be expanded and harvested in an efficient, reproducible manner that is free of human error.

Figure 2:
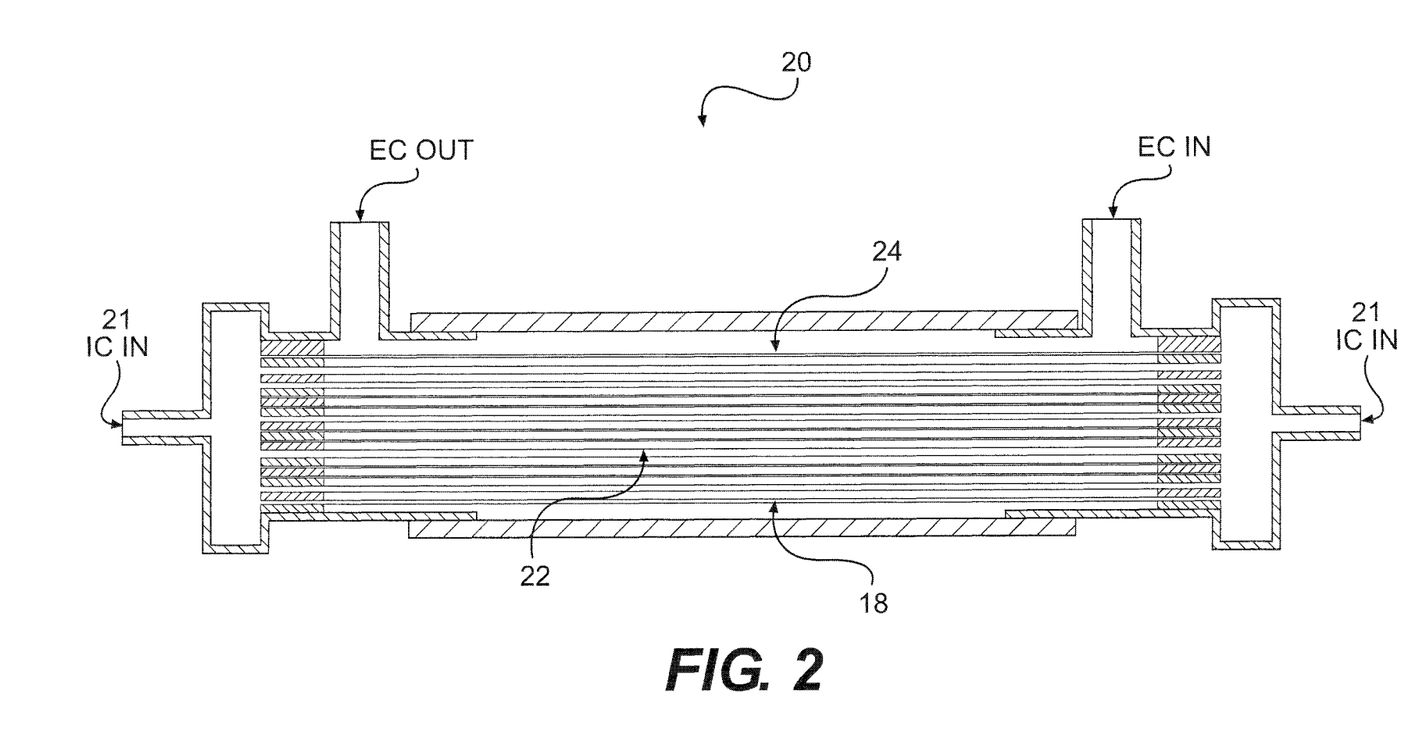
FIG. 2 is a cross-sectional view of a flexible hollow fiber bioreactor cell culture device according to the present invention.

The system is based on cell growth chamber technology. Referring to FIG. 2, a cell culture device or bioreactor 20 has a plurality of semi-permeable hollow fibers potted in a housing to create a space inside the fiber referred to as the intracapillary or IC space 22 separate from a space outside the fibers referred to as an extracapillary or EC space 24. Fluid distribution between the IC space 22 and EC space 24 occurs through the fiber pores, which can range in size from 10 Kd to 0.2 μm. Cells are placed on one side of the fiber, usually in the EC space, in a complete cell culture medium, which is usually the same medium used to expand cells prior to bioreactor inoculation (serum containing, serum-free, or protein-free medium). Cells are usually placed in the EC space when secreted protein is the desired product. In some instances, when cells are the desired product, it may be beneficial to place cells in the IC space.

Medium is perfused through bioreactor 20 by circulating it through the IC space at a fast rate, in at 21 and out at 23. The medium is a liquid containing a well defined mixture of salts, amino acids and vitamins containing one or more protein growth factors. This serves to deliver nutrients to the cell space and conversely, removes or prevents a toxic build-up of metabolic waste. Referring to FIGS. 10 and 11, during this circulation, medium is passed through an oxygenator 26 which serves to provide pH control and oxygen for the cells and conversely, remove carbon dioxide from the culture. When the bioreactor 20 contains a smaller number of cells, just after inoculation, the oxygenator or gas exchange cartridge 26 is used to provide $CO_2$ and subsequently control pH of the culture environment. As cell number increases, the oxygenator is used to remove $CO_2$ which serves to enhance acid neutralization and control the pH of the culture. It should be appreciated that other culture vessels are contemplated by the present invention.

The system 10 provides significant efficiencies and cost reduction through its disposable component and enclosed operation. As such, cell lines are contained in a closed system and continuously cultured without the need for specialized, segregated clean rooms. This fully integrated apparatus eliminates the need for cleaning and sterilization validations, as well as the need for hard plumbing associated with conventional cell culture facilities.

Figure 3:
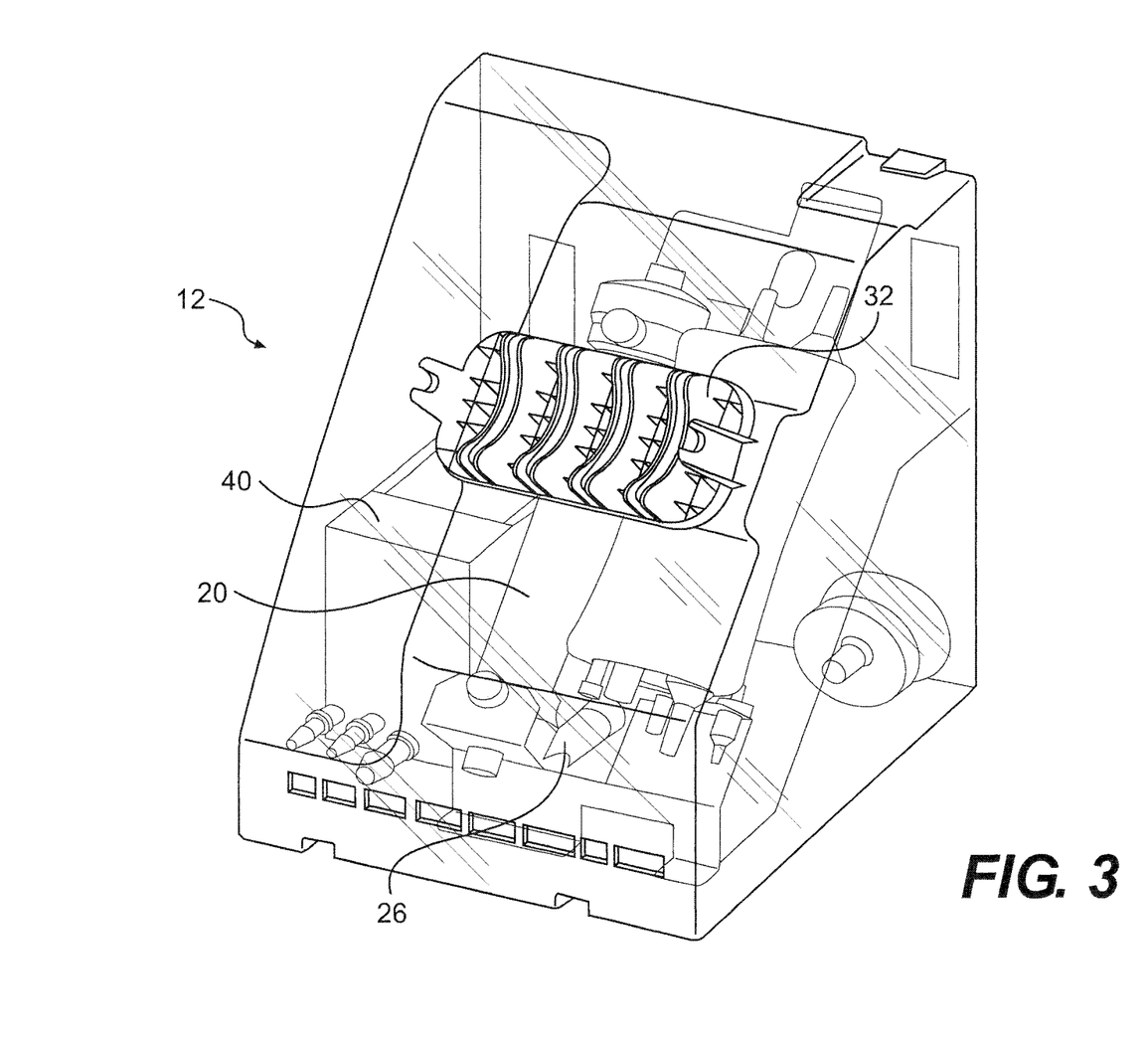
FIG. 3 is a perspective view of the disposable culture medium module of the present invention.

Referring again to FIG. 1, the system consists of two individual parts: an instrumentation base device 14 that is reusable and enclosed cultureware 12 that is used for a single production run and is disposable. The instrument provides the hardware to support cell culture growth and production in a compact package. An easy-load multiple channel peristaltic pump 16 moves fresh basal media into the cultureware, removes spent media, adds high molecular weight factor and removes product harvest. An integrated cool storage area maintains the factor and harvest at a low temperature (approximately 4° C.). Referring to FIG. 3, gas exchanger 26, in conjunction with a cultureware pH sensor 30 controls the pH of the cell culture medium. Automated tube valving drives are used to control the cultureware flow path configuration to accomplish the fluidic switching functions needed to initiate and do a successful run. Valves and sensors in the instrument control the fluid cycling in the cultureware module 12. A drive for fluid circulation is provided.

The one-time use cultureware module 12 is provided pre-sterilized. It is designed for quick loading onto the instrument. The loading of the cultureware body makes connections to the instrument. A pump cassette 32, which is physically attached to the tubing, allows the user to quickly load the pump segments. The design and layout minimizes loading errors. The cultureware enclosure 12 also provides an area that is heated to maintain cell fluid temperature.

Indicated in FIG. 3 and as shown in FIGS. 5-8, a fluid cycling unit 40 maintains fluid volumes and cycling in the bioreactor and is included in the cultureware. Sensors for fluid circulation rate, pH and a thermal well for the instrument's temperature sensor are provided. The blended gas from the instrument is routed to gas exchange cartridge 26 that provides oxygen and adds or removes carbon dioxide to the circulated fluid to support cell metabolism. A magnetically coupled pump 60 (FIG. 9) circulates fluid thru the bioreactor 20 and gas exchange cartridge 26. The bioreactor 20 provides the cell space and media component exchange and is also in the cultureware. Disposable containers for harvest collection are provided. Prior to the beginning of the culture the operator attaches a media source, factor bag and spent media container to the cultureware before running. At the conclusion of the run the harvest containers are removed or drained, the media and spent media containers are disconnected, the pump cassette is unloaded, the cultureware body is unloaded and the used cultureware is placed in a biohazard container for disposal.

The system of the present invention has application in a regulated cell culture environment. It is anticipated that autologous whole cell therapies or patient-specific proteins (vaccines) therapies, would by their nature, require the simultaneous culture of numerous cell lines in a single facility. In addition to the segregation created through this closed culture approach, the apparatus is designed to support a standard information management system (MES) protocol. This capability contributes to the creation of thorough batch records and verification of culture conditions to ensure standardization, tracking and safety of each product. This capability facilitates the multi-product concept that is pivotal to facilities involved with autologous or patient-specific products.

Figure 4:
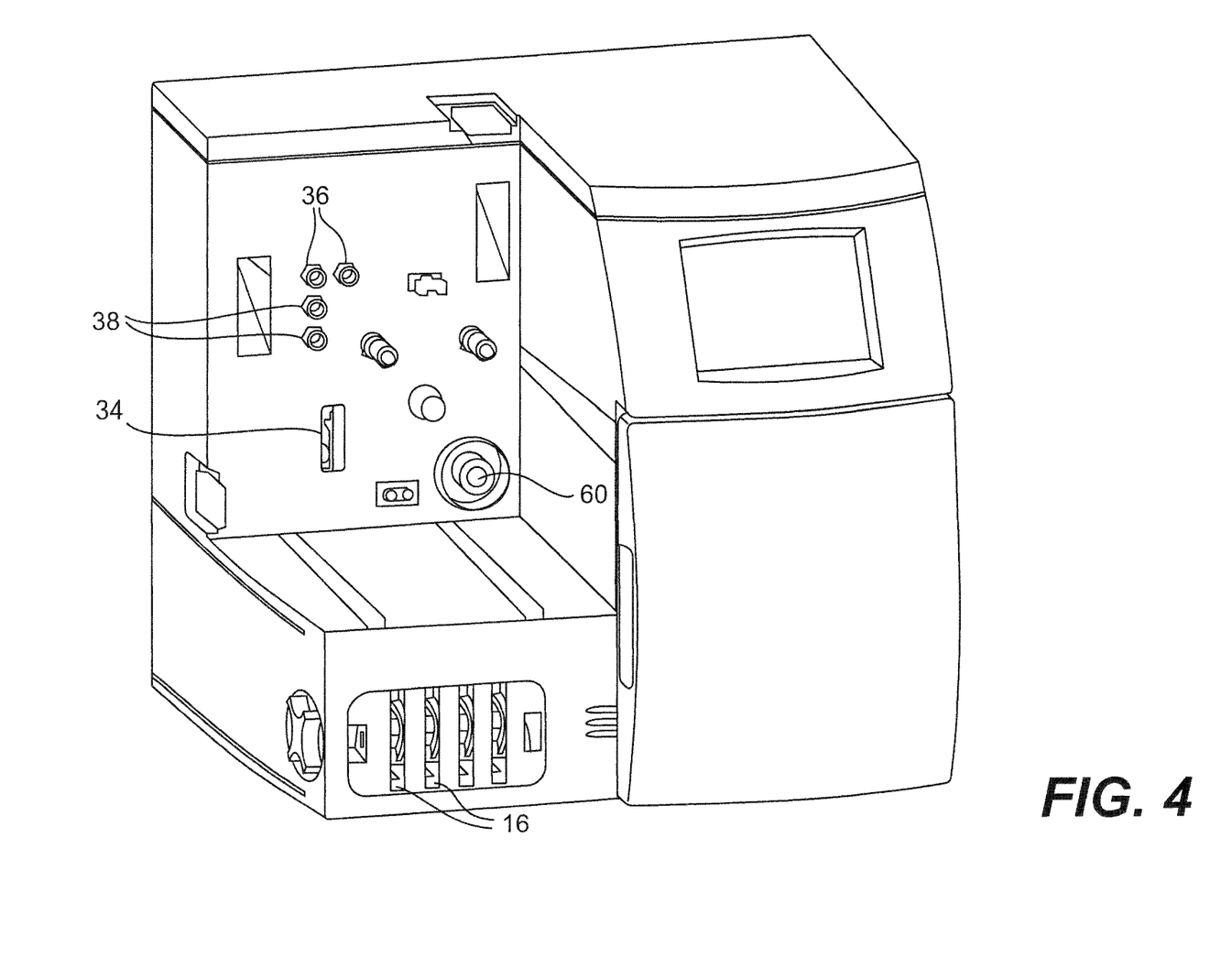
FIG. 4 is a perspective view of the instrumentation base device of the present invention.

Referring to FIGS. 3 and 4, disposable cell culture module 12 is removably attachable to device 14. The module requires multiple mechanical and electrical interfaces to the control instrumentation of device 14. Module 12 has interface features integrated into the module that mate with instrument interface features in the device to allow for a single motion installation.

As shown in FIG. 4, the interface features of device 14 include circulation pump 60 and a cycling sensor 34. Gas ports 36 communicate with gas exchanger 26. One port 36 communicates with the input to exchanger 26 and the other port 36 communicates with the output of the exchanger. As viewed from the front, left port 36 is the exchanger out and right port 36 is the exchanger input. Gas ports 38 control pressure to cycling unit 40. One port 38 communicates with the IC chamber and the other port 54 communicates with an EC pressure bag that will described further herein. The top port 54 is the IC reservoir pressurization port and the lower port 54 is the EC reservoir pressurization port.

Figure 6:
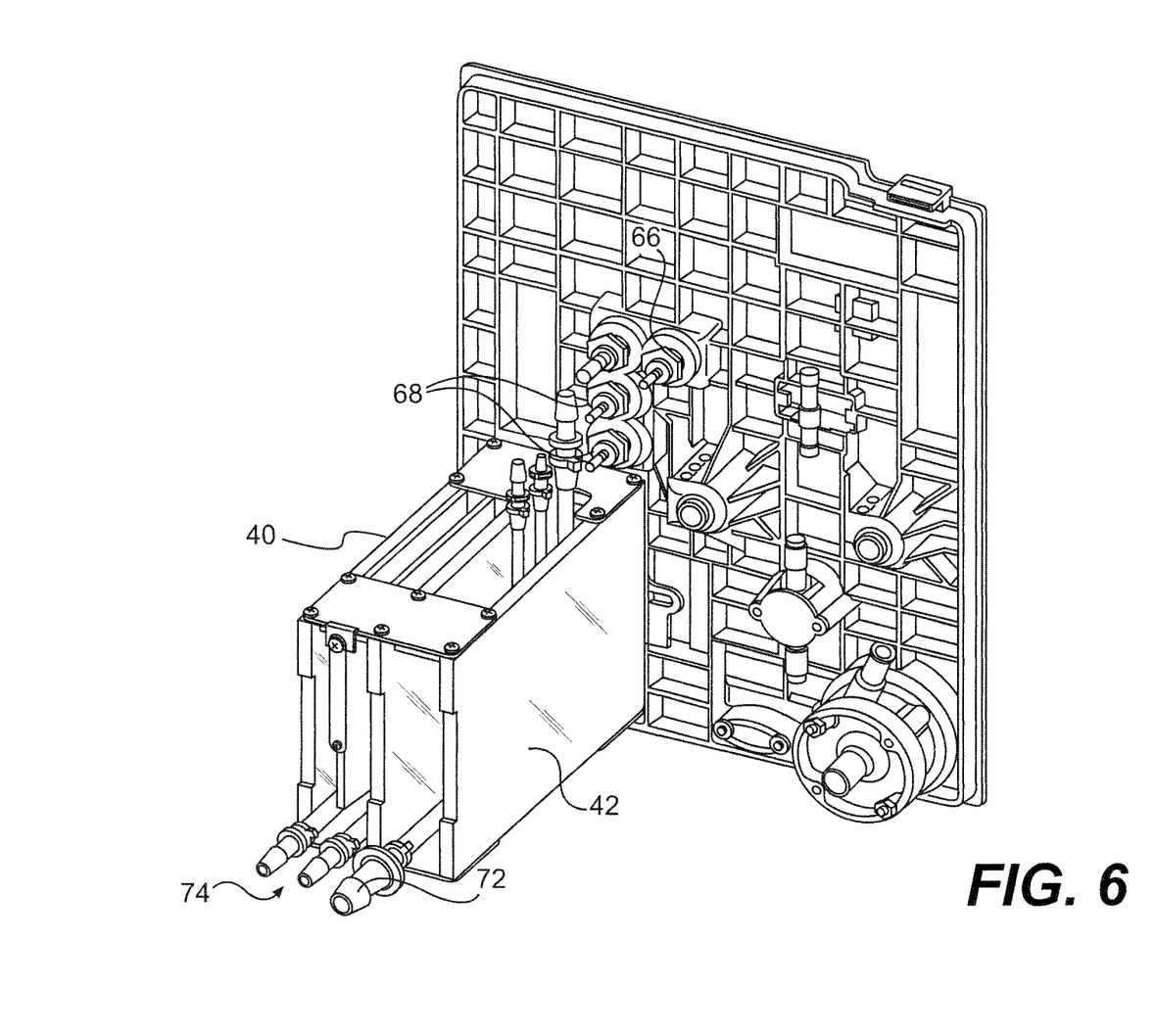
FIG. 6 is a perspective interior view of the back of the module of FIG. 5.

During installation module 12 is aligned with the connections of the device 14 and the module is placed into the operating position as shown in FIG. 1. All mating interface features are functional. Referring to FIG. 6, when installed, certain features of the module 12 interface with device 14. Gas connectors 66 and 68 engage device gas ports 36 and 38, respectively, to allow gas to enter and exit module 12. Cycling unit 40 communicates with cycling sensor 34 when the module is installed. The above mating connections facilitate the one-motion installation of the module 12 on the device.

Figure 7:
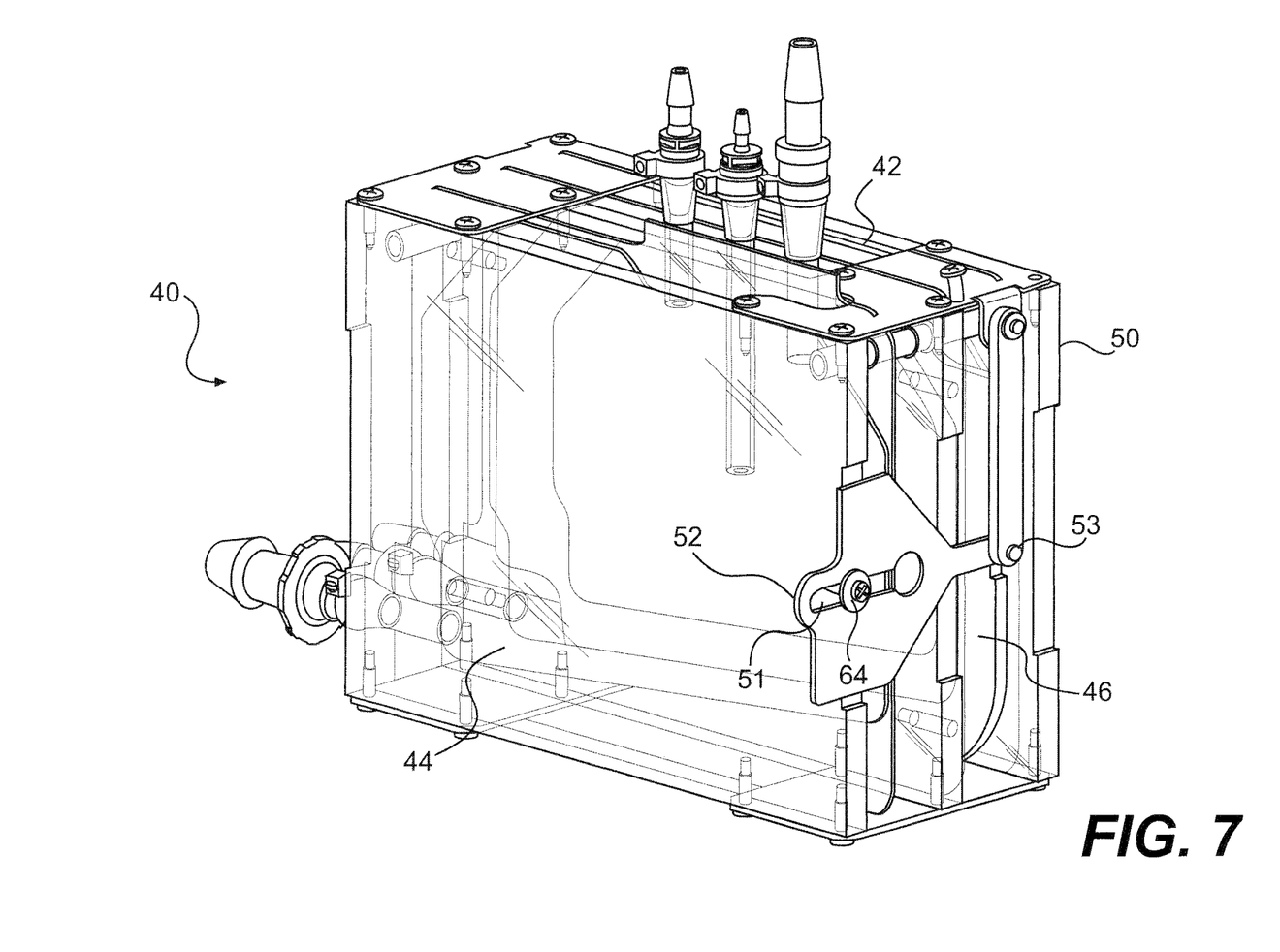
FIG. 7 is a perspective view of the extra-capillary cycling unit of the present invention.

Referring to FIGS. 4, 7, 8 and 9, valves and sensor 34 in the instrument base control the fluid cycling in the cultureware module 12. Two optical sensors 34A, 34B detect the low or high position of the cycling position sensor indicator 52 (FIG. 7). This information is used by a predictive algorithm to control the pressures applied to the IC chamber and EC pressure bag to effect cycling.

Figure 5:
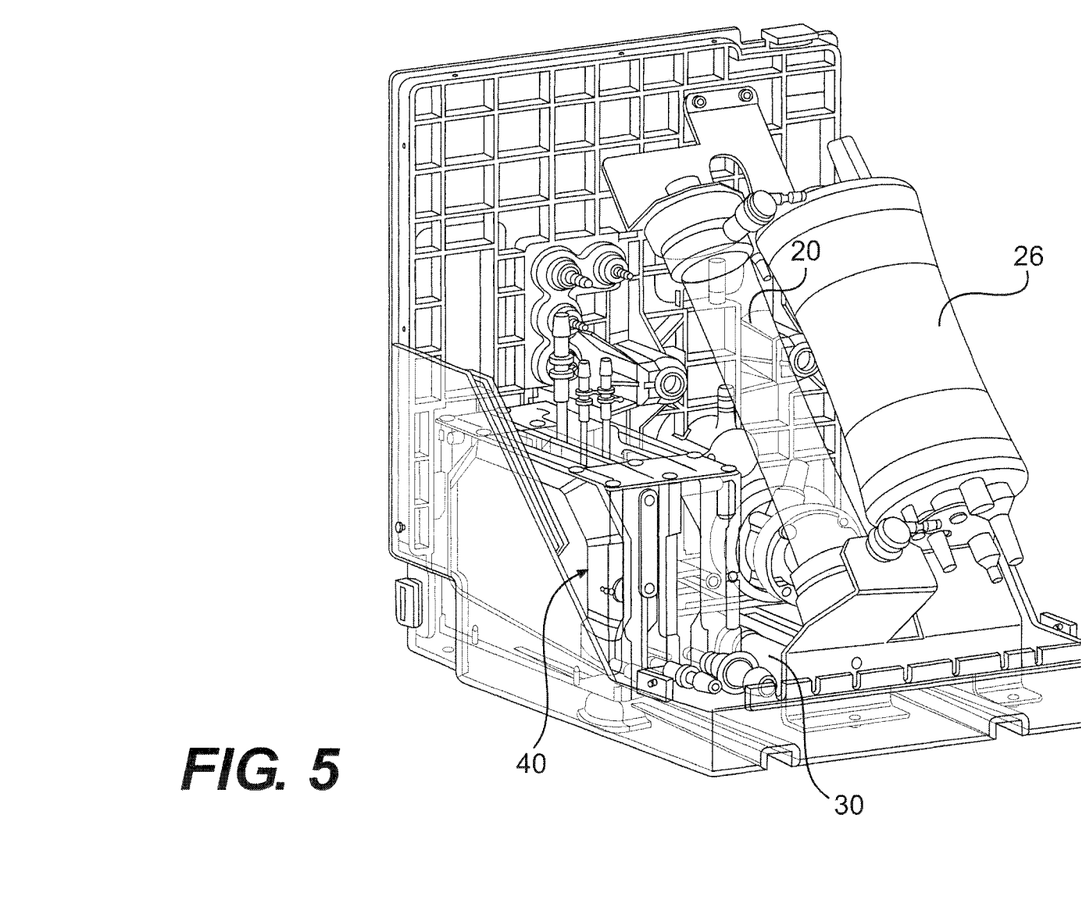
FIG. 5 is an interior view of the module of FIG. 3.

As shown in FIGS. 5-7, disposable cultureware module 12 includes fluid cycling unit 40 to maintain fluid volumes and cycling in the cell growth chamber or bioreactor 20. The present invention utilizes extra-capillary (EC) cycling in bioreactor 20 utilizing a non-rigid, first flexible EC reservoir 42 and a mechanical, second flexible reservoir 44 to cause elevated EC pressure. Reservoirs 42, 44 are movably located within housing 50, i.e., not physically attached to the housing, and are separated by a movable sensor plate 46. Although free to expand or retract within housing 50, reservoirs 42, 44 are restricted in the maximum amount of expansion by the rigid side walls of the housing 50 surrounding the same. The housing can be made from machined plastic or other comparable material. Sensor plate 46 can be made from aluminum, plastic or other comparable material. To facilitate even expansion or retraction of the respective reservoirs the side walls of housing 50 and sensor plate 46 are smooth or even.

Figure 8:
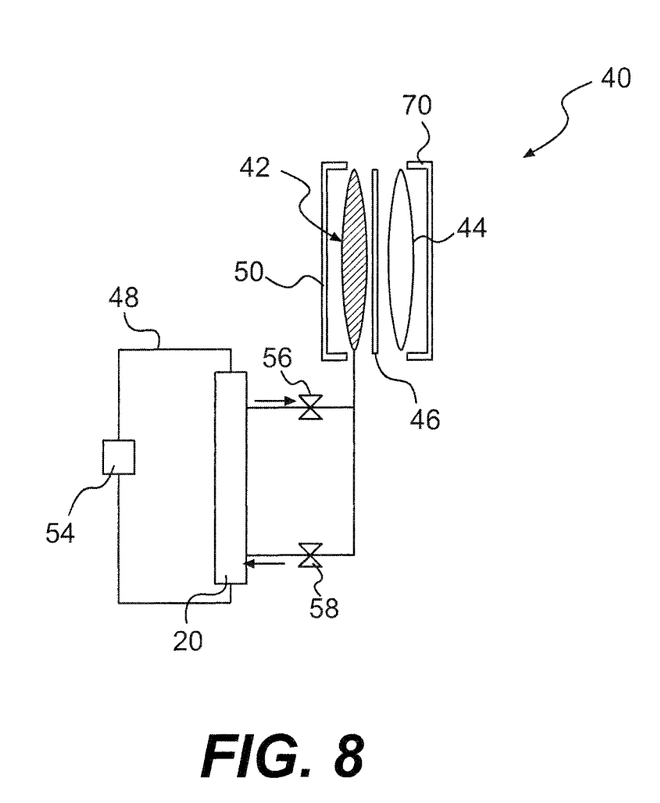
FIG. 8 is a flow diagram of the cycling unit of FIG. 7.

As shown in FIG. 8, EC cycling is achieved by utilizing the EC, non-rigid reservoir to retain the excess fluid volume associated with an EC circuit. Flexible EC reservoir 42 is fluidly connected to bioreactor 20 by connection 72 (FIG. 6) and EC circuit 76. Second flexible reservoir 44 is fluidly connected at 74 (FIG. 6) to a pressure source 70, that when expanded applies force against flexible reservoir 42 via plate 46 to provide an elevated EC pressure to cause an ultra-filtrative condition and force fluid into an intra-capillary (IC) circuit 48. Pressure source 70 can be supplied via an internal air pump contained within base device 14 and controlled via the fluid cycling control of FIG. 9.

As will be described further herein, the bioreactor fibers are permeable. A pressure differential from the EC side to the IC side of the cycling unit cause fluid to transmembrane into the opposite side and vice versa. Both reservoirs 42 and 44 can be made of a sealed flexible material, for example, a plastic film bag made from a PVC/EVA (polyvinyl/acetate ethylene vinyl acetate) co-extrusion. The circulating medium (IC) is typically a standard growth medium that consists of nutrients, vitamins, lipids, proteins, or carbohydrates required for cell proliferation or protein secretion. This medium may be substituted or altered during the course of a culture to selectively affect proliferation, protein secretion, cell phenotype, cell signaling, or facilitate cell removal from the bioreactor. The medium on the EC side is the same as on the IC side, except that high molecular weight components may be retained on the EC side because they cannot permeate the hollow fiber membrane. Cycling controls will force smaller molecular weight components of the medium from the EC side to IC side when the EC pressure is higher than the IC side.

Figure 9:
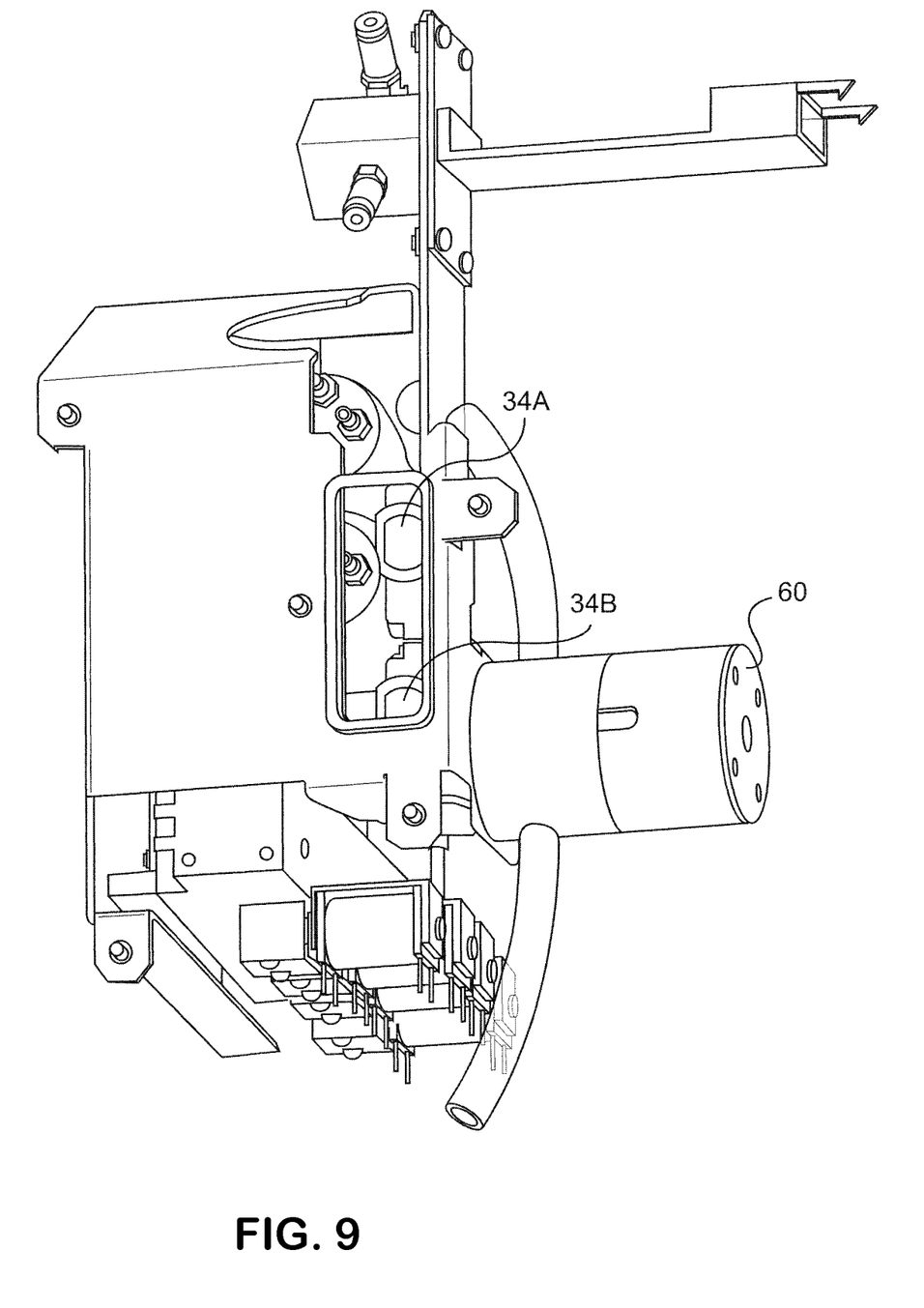
FIG. 9 is a perspective view of the fluid cycling control of the present invention.

Mechanical feed back position sensor indicator 52 is connected to sensor plate 46 and moves with the physical expansion and contraction of the first flexible reservoir 42. As shown in FIG. 7, sensor indicator 52 is attached to plate 46 at one end 53. Sensor indicator 52 includes a slot 51 located therein. As plate 46 moves sensor indicator moves and is guided by element 64 located within slot 51. Element 64 is attached to the housing. The position of indicator 52 is sensed by the position sensor 34 and is used to control the force that is applied by second flexible reservoir 44. As shown in FIG. 9, sensor 34 includes two optical sensors 34A, 34B that detect the low or high position of indicator 52. This information is used by a predictive algorithm to control the pressures applied to the IC chamber and EC pressure bag to effect cycling. Thus, if sensor 34 determines that indicator 52 is in a low position pressure applied to reservoir 42 may be reduced to enable EC reservoir to fill with fluid and vice-versa. It should be appreciated that an alternate mechanical force apparatus may be used instead of a second flexible reservoir to cause pressure changes.

As shown in FIG. 8, during operation the pressure is increased in the IC circuit 48 by pressurizing an IC reservoir 54. This pressure causes an ultra-filtrative condition that forces fluid transmembrane across the semi-permeable matrix of the bioreactor 20. The fluid is then forced through the connect tubing, through a flow control valve 56 and into the EC reservoir 42. The expanding EC reservoir 42 forces sensor plate 46 toward pressure reservoir 44 and compresses it. Sensor plate 46 activates external position sensor 52 when EC reservoir 42 has filled enough to expand to the EC upper level. External position sensor 34 senses this position and the pressure in the IC reservoir 54, is decreased and the pressure in the pressure reservoir 44 is increased. This causes an ultra-filtrative condition and forces fluid out of the EC reservoir through a control valve 58, transmembrane across the matrix of bioreactor 20 and into the IC circuit 48. The sensor plate moves the external position indicator 52 and the sensor 34 senses when EC reservoir 42 has contracted to the EC low level.

The EC cycling unit of the present invention offers fluid dynamics to cause fluid flow in the EC space, thus minimizing nutrient and metabolic waste gradients that may be detrimental to the cells. It also provides fluid level control without the use of ultrasonics or load cells and is not affected by cell debris. The flexible reservoirs of the cycling unit of the present invention are considerably less expensive and are suited for disposable applications. The sealed EC reservoir with cycling also limits contamination and isolates the cells.

In the bioreactor perfusion loop of FIG. 8, the growth media is pumped from IC reservoir 54 via pump 16, 60, circulated to gas exchange cartridge 26, pH sensor 30, hollow fiber bioreactor 20, and then back to reservoir 54. Blended gases are passed through the membrane gas exchange cartridge that oxygenates the media and removes unwanted $CO_2$. Per Henry's Law, the $CO_2$ levels in the gas phase or air side of the gas exchange cartridge 26 is in equilibrium with the liquid phase of the media. The discharge end of the gas exchange cartridge is monitored with a $CO_2$ sensor.

At present, the system of the present invention fully integrates the concept of disposable cultureware into automated process control for maintaining and expanding specialized (autologous or other) cell lines for a duration for 30 days or more. To accomplish this, the system of the present invention was designed for EC space fluid flow that enhances cell growth in high density perfusion culture, yet remains completely closed and disposable. The integrated pre-assembled cultureware, which consists of all tubing, bioreactor, oxygenator, pH probe, is enclosed in a single unit that easily snaps into the apparatus. In addition to this error-proof, quick-load design, the entire cultureware unit enclosed by the casing becomes the cell culture incubator with temperature control regulated through automated process control of the instrument. Pumps and fluid control valves facilitate disposability and error-proof installation, eliminating the possibility of technician mistakes. Finally, during the course of any culture, the closed system has restricted access except for trained and authorized personnel. Manipulations or sampling, outside of program parameters, require password and bar code access before they can be implemented.

Each unique cell line must be cultured, cell secretions harvested and purified separately. In order to manage a large number of unique cell lines, as for example might be required for the production of large numbers of autologous cell therapeutic products or large numbers of unique monoclonal antibodies, a considerable number of instruments would be needed. Compactness of the design and the amount of ancillary support resources needed become an important facilities issue. Small stirred tank systems require a means of steam generation and distribution (for steam-in-place sterilization) or autoclaves to sterilize the vessels and supporting plumbing. To support a large number of units becomes a logistics problem for the facility. The system of the present invention has no such requirement. Larger scale cell culture is historically done in segregated steps that often require separate types of equipment. Manual handling, storage and tracking is needed for all these steps as the culture expands and product is harvested. The method of the present invention integrates these steps into a continuous, fully integrated sequential process. This eliminates the handling risk and facilitates the data gathering required for thorough documentation of the entire process.

Although the present invention has been described in relation to particular embodiments thereof, many other variations and modifications and other uses will become apparent to those skilled in the art. It is preferred therefore, that the present invention be limited not by the specific disclosure herein, but only by the appended claims.

What is claimed is:

1. A cultureware module comprising:
    a cell culture chamber;
    a fluid cycling unit for maintaining and cycling fluid volumes within said cell culture chamber;
    a casing enclosing said cell culture chamber and said fluid cycling unit, and
    integrated interface features that align and mate with interface features on an instrumentation base device when said cultureware module is installed on the instrumentation base device, allowing for mechanical and electrical interfaces between said cultureware module and the instrumentation base device, wherein the instrumentation base device has valves and a sensor that control fluid cycling in said cultureware module when said cultureware module is installed on the instrumentation base device;
    wherein said fluid cycling unit comprises:
    a housing having rigid walls including a rigid side wall;
    a flexible fluid reservoir movably disposed in said housing, said flexible fluid reservoir being in fluid communication with said cell growth chamber;
    a mechanical force apparatus movably located in said housing and adjacent to said flexible fluid reservoir;
    a single plate movably disposed in said housing between said flexible fluid reservoir and said mechanical force apparatus, wherein said flexible fluid reservoir, said mechanical force apparatus, and said single plate are surrounded by said rigid walls of said housing, wherein said mechanical force apparatus moves against said single plate, thereby applying force against said single plate, and moves said single plate in relation to said flexible fluid reservoir, contacting said flexible fluid reservoir, to cause fluid cycling and maintain fluid volumes in said cell growth chamber; and
    a sensor indicator connected to said single plate, wherein physical expansion and contraction of said flexible fluid reservoir moves said sensor indicator within said housing such that the position of said sensor indicator can be sensed by the sensor, wherein the sensor is in communication with said mechanical force apparatus when said cultureware module is installed on the instrumentation base device, controlling the force that is applied by said mechanical force apparatus to said flexible fluid reservoir through said single plate, and wherein maximum physical expansion of said flexible fluid reservoir is restricted by said rigid side wall of said housing.

2. The cultureware module of claim 1, wherein said cell growth chamber comprises a hollow fiber bioreactor that provides cell space and media component exchange.

3. The cultureware module of claim 1, wherein the sensor comprises two optical sensors.

4. The cultureware module of claim 2, wherein said hollow fiber bioreactor has a plurality of semi-permeable hollow fibers potted in a housing, an intracapillary space within said fibers, and an extracapillary space outside said fibers, and wherein said intracapillary space accommodates medium that is circulated through said intracapillary space when said cultureware module is installed on the instrumentation base device and in operation.

5. The cultureware module of claim 1, wherein said integrated interface features of said cultureware module allow for a single-motion installation on the instrument base device.

6. A method for fluid cycling in a cell culture chamber, comprising the steps of:
    providing said cultureware module of claim 1,
    providing an instrumentation base device comprising interface features, and valves and a sensor that control fluid cycling in said cultureware module when said cultureware module is installed on said instrumentation base device, wherein said sensor is in communication with said mechanical force apparatus, and wherein said sensor indicator is in communication with said sensor;
    installing said cultureware module on said instrumentation base device by aligning and mating said integrated interface features on said cultureware module with said interface features on said instrumentation base device, resulting in said cultureware module being removably attached to said instrumentation base device, and providing mechanical and electrical interfaces between said cultureware module and said instrumentation base device;
    activating said mechanical force apparatus, moving said single plate to expand or contract said flexible fluid reservoir; and
    cycling the fluid through the cell culture chamber.

7. The method of claim 6, wherein the step of cycling the fluid comprises moving the fluid through a cell space of said cell culture chamber and exchanging media components.

8. The method of claim 7, further comprising the step of activating said sensor with said sensor indicator, wherein physical expansion and contraction of said flexible fluid reservoir moves said sensor indicator within said housing to control activation of said mechanical force apparatus.

9. The method of claim 6, wherein said sensor comprises two optical sensors.

10. The method of claim 6, wherein the fluid comprises cell culture medium.

11. The method of claim 6, wherein said cell growth chamber comprises a hollow fiber bioreactor that provides cell space and media component exchange.

12. The method of claim 11, wherein said hollow fiber bioreactor has a plurality of semi-permeable hollow fibers potted in a housing, an intracapillary space within said fibers, and an extracapillary space outside said fibers, and wherein said intracapillary space accommodates medium that is circulated through said intracapillary space when said cultureware module is installed on the instrumentation base device and in operation.

13. The method of claim 6, further comprising, after a production run, harvesting cells or cell products produced in the cell culture chamber, and disposing of said cultureware module.

* * * * *